United States Patent [19]

Vahteristo et al.

[11] Patent Number: 5,952,534
[45] Date of Patent: Sep. 14, 1999

[54] MANUFACTURING OF 2,6-DIMETHYLNAPHTHALENE

[75] Inventors: Kari Vahteristo, Lappeenranta; Erkki Halme; Salme Koskimies, both of Helsinki, all of Finland; Sigmund M. Csicsery, Lafayette, Calif.; Markku Laatikainen, Pulp; Vesa Niemi, Porvoo, both of Finland

[73] Assignee: Optatech Oy, Espoo, Finland

[21] Appl. No.: 08/973,864

[22] PCT Filed: Jul. 4, 1996

[86] PCT No.: PCT/FI96/00395

§ 371 Date: Mar. 20, 1998

§ 102(e) Date: Mar. 20, 1998

[87] PCT Pub. No.: WO97/02225

PCT Pub. Date: Jan. 23, 1997

[30] Foreign Application Priority Data

Jul. 5, 1995 [FI] Finland ..................... 953319

[51] Int. Cl.[6] ................... C07C 15/24
[52] U.S. Cl. ............ 585/320; 585/411; 585/418; 585/420; 585/421
[58] Field of Search ............... 585/320, 411, 585/418, 420, 421

[56] References Cited

U.S. PATENT DOCUMENTS

| 3,931,348 | 1/1976 | Taniguchi et al. | 585/411 |
| 5,276,230 | 1/1994 | Inamasa et al. | 585/320 |
| 5,321,178 | 6/1994 | Inamasa et al. | 585/411 |

FOREIGN PATENT DOCUMENTS

| 0362507 A3 | 4/1990 | European Pat. Off. . |
| 0362651 A3 | 4/1990 | European Pat. Off. . |
| 0430714 A2 | 6/1991 | European Pat. Off. . |
| 0546266 A1 | 6/1993 | European Pat. Off. . |
| 7309789 | 11/1995 | Japan . |
| 14448136 | 9/1976 | United Kingdom . |

OTHER PUBLICATIONS

Chemical Abstracts, vol. 84 (1976), 4735a Japan 75–17,983, No Month Available.

*Primary Examiner*—Walter D. Griffin
*Attorney, Agent, or Firm*—Oblon, Spivak McClelland, Maier & Neustadt, P.C.

[57] ABSTRACT

The invention is related to a process for making 2,6-dimethylnaphthalene from p-xylene and 1- or 2-butene or butadiene via 1-(p-tolyl)-2-methylbutane or 1-(p-tolyl)-2-methylbutane. 2,6-dimethylnaphthalene can be used for making polyethylenenaphthalate.

7 Claims, No Drawings

MANUFACTURING OF 2,6-DIMETHYLNAPHTHALENE

TECHNICAL AREA

The invention is related to the manufacturing of 2,6-dimethylnaphthalene from p-xylene and 1- or 2-butene or butadiene via the intermediates 1-(p-tolyl)-2-methylbutane or 1-(p-tolyl)-2-methylbutene. 2,6-dimethylnaphthalene can be used as a raw-material for manufacturing of polyethylenenaphthalate.

TECHNICAL BACKGROUND

Polyethylenenaphthalate (PEN) has got very good mechanical strength and heat resistance. Its known manufacturing processes, however, have not been competitive.

Polyethylenenaphthalate is made from 2,6-naphthalenedicarboxylic acid, which is made by oxidizing 2,6-dimethylnaphthalene. Nowadays 2,6-dimethylnaphthalene is separated from hydrocarbon mixtures. In this way only small amounts are obtained. Furthermore also the separation and purification is difficult.

It has also been suggested to manufacture 2,6-dimethylnaphthalene by cyclization of 1-(p-tolyl)-2-methylbutane and/or 1-(p-tolyl)-2-methylbutene.

The manufacturing of 2,6-dimethylnaphthalene has been described in many patents. In some of these patents also the manufacturing of 1-(p-tolyl)-2-methylbutane and/or 1-(p-tolyl)-2-methylbutene is described. In some patents also the use of chromium oxide/aluminum oxide and its impregnation with potassium is mentioned.

In GB-1448136 (1976) the manufacturing of 1-(p-tolyl)-2-methylbutane and/or 1-(p-tolyl)-2-methylbutene in many different ways is described. In most cases one component is p-xylene, the methyl group of which is alkylated with butene using a basic catalyst. In three examples the manufacturing of 2,6-dimethylnaphthalene using a $Cr_2O_3/Al_2O_3$-catalyst poisoned with potassium is described. In the claims the amount of impregnated alkali metal oxide is 0.1–20 wt. % but in the examples the amounts of potassium are 2.1 and 3.5 wt. %. However, 3.1% and 5.0% of the total amount of dimethylnaphthalene is 2,7-dimethylnaphthalene which is very difficult to separate.

In EP430714A (1990) a chromium oxide/aluminum oxide catalyst poisoned with potassium is mentioned in one example but in the claims only the oxides are mentioned but not the amounts. In one example the components K:Cr:AL are in the proportions 7:11:100. In the same example the proportion of 2,6-dimethylnaphthalene of the total amount of dimethylnaphthalenes is 98.6%.

In EP-362507A (1989) p-xylene, 1-butene and carbon monoxide are used as raw-materials when making 1-(p-tolyl)-2-methylbutane and/or 1-(p-tolyl)-2-methylbutene. When making the 2,6-dimethylnaphthalene $Cr_2O_3$-5% $K_2O$-$Al_2O_3$ is used as catalyst The selectivity of 2,6-dimethylnaphthalene was reported to be 71%. Nothing is mentioned about the purity of the product. In the claims only aluminum oxide and silicon oxide are mentioned.

EP-362651A (1989) is almost the same as EP-362507A regarding the dehydrocyclization reaction. The only difference is that m-xylene, propylene and carbon monoxide are used for making 2,4-dimethyl-isobutyrophenone, which is cyclisized to 2,6-dimethylnaphthalene.

In the patents mentioned above nothing is said about C12-alkylindanes and -indenes which are very difficult to separate because they are boiling at almost the same temperature as the dimethylnaphthalenes.

DESCRIPTION OF THE INVENTION

Now the process described in claim 1 has been invented. Some preferable process alternatives are presented in the claims.

The reactions according to the invented process are described below:

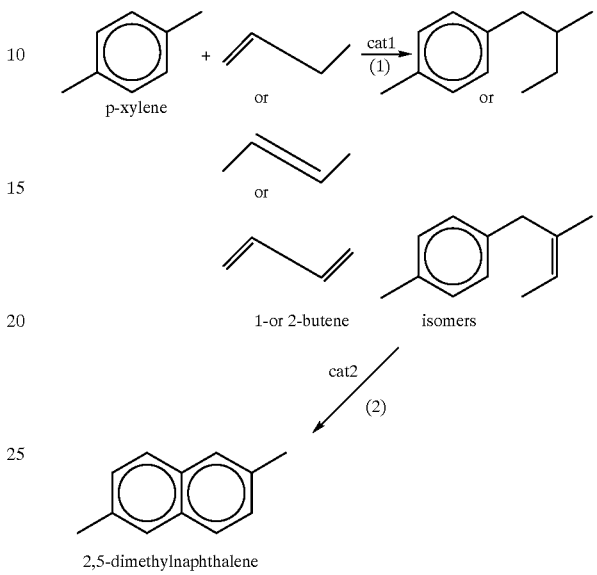

In reaction step 1 the alkylation of the benzyl side chain is done so that the amount of n-alkyl compounds is minimized. For this purpose some basic catalysts are therefore most appropriate.

In reaction step 2 on the other hand the aromatic dehydrocyclization is done using a $Cr_2O_3$-, $V_2O_5$- or Pt-catalyst.

According to the first aspect of the invention p-xylene is reacted with butene or butadiene to p-(2-methylbutyl) toluene or p-(2-methylbutyl) toluene using an alkali metal as catalyst and this catalyst is preferably attached to a suitable support. As a catalyst one can use for instance potassium dispersed on the surface of graphite or sodium mixed with potassium carbonate at a high temperature.

According to the second aspect of the invention p-(2-methylbutyl) toluene or p-(2-methylbuthenyl)toluene are dehydrocyclicized selectively to 2,6-dimethylnaphthalene in the presence of a catalyst. As catalyst one can use for instance chromium oxide (for instance $Cr_2O_3/Al_2O_3$) or platinum (for instance Pt/C, Pt/SiO$_2$ or Pt/BaL-zeolite). The best choice is, however, to use a $Cr_2O_3$-catalyst modified with potassium, for instance $Cr_2O_3/Al_2O_3$ impregnated with $K_2CO_3$. By impregnating the catalyst with potassium fragmentation becomes more favoured. Every methyl-group which is split off decreases the boiling point about 20° C. By fragmenting C12-alkyl-indanes and -indenes they can easily be separated from 2,6 -dimethylnaphthalene. In this way 2,6-dimethylnaphthalene can be manufactured selectively and profitably.

The amount of potassium in the catalyst can be 0.5–20 wt. % but preferably 4–10 wt. %.

Below are some non-limiting examples which describe the invention:

EXAMPLE 1

Molten potassium was dissolved in xylene at 70° C. (mixing at 200 RPM) and dispersed on the surface of graphite (weight ratio of potassium:graphite:xylene was 1:1:10). To the same autoclave were then added 1- or 2-butene or butadiene in a semi-batch mode during 6–8 hours. The reaction product was composed of 79% C6-alkyl (or alkenyl)-benzenes with a p-(2-methyl)buthyl(or buthenyl)toluene content of 67 wt. %. p-n-penthyltoluene was the biggest component which was not wanted but it was very easy to separate by distillation.

EXAMPLE 2

The $Cr_2O_3/Al_2O_3$-catalyst was treated with a water solution of $K_2CO_3$ so that the potassium concentration of the catalyst was 4.7 wt %. This mixture was then kept at −20° C. and dried in vacuum for 3 days. Then it was calcined in a reactor tube at 500° C.

EXAMPLE 3

The $Cr_2O_3/Al_2O_3$-catalyst (Chromium content 15%; Cr/Al, 0.12) was treated with a water solution of $K_2CO_3$ so that the potassium concentration of the catalyst was 8.3 wt. %. This mixture was then dried at room temperature for 20 hours and after that in a drying oven at 100° C. The calcination was done in a reactor tube at 500° C.

EXAMPLE 4

The $Cr_2O_3/Al_2O_3$-catalyst was treated with a water solution of $K_2CO_3$ so that the potassium concentration of the catalyst was 2.1 and 8.1 wt. %. This mixture was then dried at 100° C. for 2 hours and calcined at 500° C.

EXAMPLE 5

A $SiO_2$-carrier (Grace $SiO_2$ 432) was dried and pre-calcined at 300° C. Pt $(acac)_2$ was then dissolved in THF by heating slightly and the dried $SiO_2$-carrier was impregnated with this Pt-THF-solution at 120° C. The impregnated $SiO_2$-carrier was aged for 1 day after which it was calcined at 300° C. for 4 h.

EXAMPLE 6

The $Pt/SiO_2$-catalyst (Pt 1%) made according to Example 5 was put into a 4 ml (9 mm inner diameter) quartz tube which was used as a reactor. Then 96% 1-(p-tolyl)-2-methylbutane (LHSV, 0.25 $h^{-1}$) with hydrogen as a carrier gas (3 mol H2/1 mol 1-(p-tolyl)-2-methylbutane) was pumped through the reactor. The reaction conditions were: temperature 510° C.; pressure 1 bar; contact time 5.2 s. A sample was taken 1 h after starting the experiment and the results are presented below:
Conversion 58.2%
Selectivity of converted 1-(p-tolyl)-2-methylbutane (mol %)

| C6–C11 | 39.4 |
|---|---|
| 1-(p-tolyl)-2-methylbutene | 14.2 |
| C12-alkyl-indanes and -indenes | 8.1 |
| 2 - methylnaphthalene | 10.1 |
| dimethylnaphthalenes | 24.9 |
| (2,6 - dimethylnaphthalene | 23.6) |

EXAMPLE 7

The catalyst made according to Example 2 was put into a 4 ml (9 mm inner diameter) steel tube which was used as a reactor. Then 96% 1-(p-tolyl)-2-methylbutane (LHSV, 0.25 $h^{-1}$) with nitrogene as a carrier gas (1.8 mol N2/1 mol 1-(p-tolyl)-2-methylbutane) was pumped through the reactor. The reaction conditions were: temperature 510° C.; pressure 1 bar; contact time 7.7 s. A sample was taken 1 h after starting the experiment and the results are presented below:
Conversion 83.4%
Selectivity of converted 1-(p-tolyl)-2-methylbutane (mol %)

| C6–C11 | 72.9 |
|---|---|
| 1-(p-tolyl)-2-methylbutenes | 2.1 |
| C12-alkyl-indanes and -indenes | 0.4 |
| 2 - methylnaphthalene | 5.7 |
| dimethylnaphthalenes | 18.5 |
| (2,6 - dimethylnaphthalene | 18.3) |

EXAMPLE 8

The dehydrocyclization was done according to Example 6 except for the following changes: LHSV, 0.5 $h^{-1}$; contact time, 4 s; 1.3 mol H2/1 mol 1-(p-tolyl)-2-methylbutane. The results are presented below:
Conversion 58.2%
Selectivity of converted 1-(p-tolyl)-2-methylbutane (mol %)

| C6–C11 | 70.8 |
|---|---|
| 1-(p-tolyl)-2-methylbutane | 5.2 |
| C12-alkyl-indanes and -indenes | 1.4 |
| 2 - methylnaphthalene | 3.8 |
| dimethylnaphthalenes | 16.7 |
| (2,6 - dimethylnaphthalene | 16.2) |

EXAMPLE 9

The dehydrocyclization was done according to Example 6 except for the following changes: LHSV, 1.0 $h^{-1}$; contact time, 1.9 s. The results are presented below:
Conversion 38.3%
Selectivity of converted 1-(p-tolyl)-2-methylbutane (mol %)

| C6–C11 | 64.7 |
|---|---|
| 1-(p-tolyl)-2-methylbutenes | 11.9 |
| C12-alkyl-indanes and -indenes | 3.6 |
| 2 - methylnaphthalene | 2.3 |
| dimethylnaphthalenes | 15.6 |
| (2,6 - dimethylnaphthalene | 14.9) |

EXAMPLE 10

The dehydrocyclization was done according to Example 8 except for the catalyst which was pure $Cr_2O_3/Al_2O_3$. The results are presented below:
Conversion 54.8%
Selectivity of converted 1-(p-tolyl)-2-methylbutane (mol %)

| C6–C11 | 32.9 |
|---|---|
| 1-(p-tolyl)-2-methylbutenes | 21.5 |
| C12-alkyl-indanes and -indenes | 6.4 |
| 2 - methylnaphthalene | 1.2 |

-continued

| | |
|---|---|
| dimethylnaphtalenes | 35.4 |
| (2,6 - dimethylnaphthalene | 33.8) |

EXAMPLE 11

The dehydrocyclization was done according to Example 9 except for the following changes: temperature 450° C.; contact time 7.3 s. The results are presented below:
Conversion 54.7%
Selectivity of converted 1-(p-tolyl)-2-methylbutane (mol %)

| | |
|---|---|
| C6–C11 | 39.0 |
| 1-(p-tolyl)-2-methylbutenes | 33.9 |
| C12-alkyl-indanes and -indenes | 6.0 |
| 2 - methylnaphthalenes | 0.3 |
| dimethylnaphtalenes | 16.2 |
| (2,6 - dimethylnaphthalene | 15.3) |

EXAMPLE 12

The catalyst made in Example 3 was put into a 4 ml (9 mm inner diameter) quartz tube which was used as a reactor. Then 96% 1-(p-tolyl)-2-methylbutane (LHSV, 1.0 h$^{-1}$) with nitrogene as a carrier gas (1.8 mol N$_2$/1 mol 1-(p-tolyl)-2-methylbutane) was pumped through the reactor. The reaction conditions were: temperature 510° C.; pressure 1 bar; contact time 1.7 s. A sample was taken 1 h after starting the experiment and the results are presented below:
Conversion 26.7%
Selectivity of converted 1-(p-tolyl)-2-methylbutane (mol %)

| | |
|---|---|
| C6–C11 | 67.6 |
| 1-(p-tolyl)-2-methylbutenes | 13.7 |
| C12-alkyl-indanes and -indenes | 2.8 |
| 2 - methylnaphthalene | 2.1 |
| dimethylnaphtalenes | 11.5 |
| (2,6 - dimethylnaphthalene | 11.5) |

EXAMPLE 13

The dehydrocyclization was done according to Example 12 except for the following changes: temperature 450° C.; LHSV 0.3 h$^{-1}$; contact time 7.3 s. The results are presented below:
Conversion: 22.6%
Selectivity of converted 1-(p-tolyl)-2-methylbutane (mol %)

| | |
|---|---|
| C6–C11 | 63.3 |
| 1-(p-tolyl)-2-methylbutenes | 22.0 |
| C12-alkyl-indanes and -indenes | 0.6 |
| 2 - methylnaphthalene | 0.3 |
| dimethylnaphtalenes | 10.8 |
| (2,6 - dimethylnaphthalene | 10.4) |

EXAMPLE 14

The dehydrocyclization was done according to Example 6 except for the LHSV which was 0.5 h$^{-1}$. The results are presented below:
Conversion: 42.0%
Selectivity of converted 1-(p-tolyl)-2-methylbutane (mol %)

| | |
|---|---|
| C6–C11 | 33.5 |
| 1-(p-tolyl)-2-methylbutenes | 27.3 |
| C12-alkyl-indanes and -indenes | 9.8 |
| 2 - methylnaphthalene | 4.0 |
| dimethylnaphtalenes | 19.2 |
| (2,6 - dimethylnaphthalene | 18.2) |

EXAMPLE 15

The dehydrocyclization was done according to Example 6 except for the LHSV which was 1 h$^{-1}$. The results are presented below:
Conversion: 58.2%
Selectivity of converted 1-(p-tolyl)-2-methylbutane (mol %)

| | |
|---|---|
| C6–C11 | 28.6 |
| 1-(p-tolyl)-2-methylbutenes | 38.6 |
| C12-alkyl-indanes and -indenes | 11.3 |
| 2 - methylnaphthalene | 2.0 |
| dimethylnaphtalenes | 14.4 |
| (2,6 - dimethylnaphthalene | 13.9) |

EXAMPLE 16

The Pt/BaL-zeolite catalyst was put into a 3 ml (9 mm inner diameter) quartz tube which was used as a reactor. Then 96% 1-(p-tolyl)-2-methylbutane (LHSV, 1.7 h$^{-1}$) with hydrogene as carrier gas (3 mol H$_2$/1 mol 1-(p-tolyl)-2-methylbutane). The reaction conditions were: temperature 510° C.; pressure 1 bar; contact time 0.8 s. A sample was taken 1 h after starting the experiment and the results are presented below:
Conversion 71.4%
Selectivity of converted 1-(p-tolyl)-2-methylbutane (mol %)

| | |
|---|---|
| C6–C11 | 40.2 |
| 1-(p-tolyl)-2-methylbutenes | 6.2 |
| C12-alkyl-indanes and -indenes | 3.3 |
| 2 - methylnaphthalene | 17.6 |
| dimethylnaphtalenes | 14.9 |
| (2,6 - dimethylnaphthalene | 13.5) |

We claim:

1. A process for preparing 2,6-dimethylnaphthalene, comprising:

contacting, at reaction conditions, p-xylene and butene or butadiene with a catalyst comprising supported potassium or sodium, in a first step to produce an intermediate of p-(2-methylbutyl)toluene or p-(2-methylbutenyl)toluene, and contacting, in a second step, the intermediate with a catalyst comprising supported chromium oxide modified with K$_2$CO$_3$ to produce 2,6-dimethylnaphthalene with simultaneous fragmentation of C12-alkylindanes or -indenes.

2. Process according to claim 1, wherein the catalyst used in the first step is potassium dispersed on the surface of graphite or sodium mixed with potassium carbonate.

3. Process according to claim 1, wherein the catalyst used in the second step is $Cr_2O_3$ supported on $Al_2O_3$ and impregnated with $K_2CO_3$.

4. Process according to claim 3, wherein the concentration of potassium in the catalyst used in the second step is 0.5–20 wt. %.

5. Process according to claim 4, wherein the concentration of potassium in the catalyst used in the second step is 8.1–8.3 wt. %.

6. The process of claim 4, wherein the concentration of potassium in the catalyst used in the second step is 4–10 wt. %.

7. A process for preparing 2,6-dimethylnaphthalene, comprising:

contacting p-(2-methylbutyl)toluene or p-(2-methylbutenyl)toluene under dehydrocyclization conditions with a catalyst comprising supported chromium oxide modified with $K_2CO_3$ to produce 2,6-dimethylnaphthalene with simultaneous fragmentation of C12-alkylindanes or -indenes.

* * * * *